(12) United States Patent
Bar-Yoseph et al.

(10) Patent No.: US 8,623,825 B2
(45) Date of Patent: Jan. 7, 2014

(54) EDIBLE FAT COMPOSITION FOR ENHANCING BONE STRENGTH

(75) Inventors: Fabiana Bar-Yoseph, Haifia (IL); Dori Pelled, Hod Hasharon (IL); Yael Lifshitz, Zihron Yaakov (IL)

(73) Assignee: Enzymotec Ltd., Migdal Ha 'Emeq (IL)

( * ) Notice: Subject to any disclaimer, the term of this patent is extended or adjusted under 35 U.S.C. 154(b) by 508 days.

(21) Appl. No.: 12/671,678

(22) PCT Filed: Jul. 31, 2008

(86) PCT No.: PCT/IL2008/001053
§ 371 (c)(1),
(2), (4) Date: Jun. 17, 2011

(87) PCT Pub. No.: WO2009/016632
PCT Pub. Date: Feb. 5, 2009

(65) Prior Publication Data
US 2011/0244071 A1    Oct. 6, 2011

(30) Foreign Application Priority Data
Aug. 1, 2007    (IL) .......................................... 184982

(51) Int. Cl.
*A61K 38/00* (2006.01)
(52) U.S. Cl.
USPC ...................................................... 514/16.7
(58) Field of Classification Search
None
See application file for complete search history.

(56) References Cited

U.S. PATENT DOCUMENTS

2004/0062820 A1    4/2004    Lasekan et al.

FOREIGN PATENT DOCUMENTS

| WO | 2005/036978 A1 | 4/2005 |
|---|---|---|
| WO | 2005/036987 A1 | 4/2005 |
| WO | 2005/037373 A1 | 4/2005 |
| WO | WO 2005036987 A1 * | 4/2005 |

OTHER PUBLICATIONS

International Search Report issued in International Appln. No. PCT/IL2008/001053 mailed on Dec. 3, 2008.
Majumdar, "Current Technologies in the Evaluation of Bone Architecture", Current Osteoporosis Reports 2003, II:105-109, Current Science Inc. ISSN 1544-1873 Copyright © 2003 by Current Science Inc.
Turner, "Biomechanics of Bone: Determinants of Skeletal Fragility and Bone Quality", Osteoporos Int (2002) 13:97-104 © 2002 International Osteoporosis Foundation and National Osteoporosis Foundation.

(Continued)

*Primary Examiner* — Anand Desai
*Assistant Examiner* — Melissa Mercier
(74) *Attorney, Agent, or Firm* — John P. White; Cooper & Dunham LLP

(57) ABSTRACT

Disclosed is describes a method of increasing bone strength and/or increasing bone resistance to bending and/or improving bone architecture and/or maintaining bone status in a human, comprising administering to said human a composition comprising a fat source, wherein said fat source is a triglyceride fat source comprising triglycerides with 15-55% palmitic acid moieties out of the total fatty acids, and wherein the level of palmitic acid moieties at the sn-2 position of the glycerol backbone is at least 30% (w/w) of total palmitic acid. Said method is particularly intended for subjects at risk of impaired bone strength. Further disclosed is said fat source, as well as food articles and a commercial package comprising the same.

8 Claims, 1 Drawing Sheet

(56) References Cited

OTHER PUBLICATIONS

Gilsanz, "Bone density in children: a review of the available techniques and indications", European Journal of Radiology 26 (1998), pp. 177-182.

Takeda et al., "A Study on Spontaneously Obese Rat (Minko Rat) with Abnormal Lipid Metabolism, Strength and Mineral Concentrations in Bone", Journal of the American College of Nutrition, vol. 23, No. 6, 712S-714S (2004).

Riggs et al., "Effect of Fluoride Treatment on the Fracture Rate in Postmenopausal Women with Osteoporosis", The New England Journal of Medicine, vol. 322 No. 12, Mar. 22, 1990, pp. 802-809.

Divittorio et al., "Examining the Relationship Between Bone Mineral Density and Fracture Risk Reduction During Pharmacologic Treatment of Osteoporosis", Pharmacotherapy vol. 26, Nov. 1, 2006, pp. 104-114.

Allen et al., "Raloxifene enhnaces vertebral mechanical properties independent of bone density", Bone 36 (2006), pp. 1130-1135.

Turner et al., "Basic Biomechanical Measurements of Bone: A Tutorial", Bone, 14, pp. 595-608 (1993).

Currey et al., "The Mechanical Properties of Bone Tissue in Children", The Journal of Bone and Joint Surgery (1975), pp. 810-814.

Petit et al., "Examining the developing bone: What do we measure and how do we do it?", Journal of Musculoskelet Neuronal Interact 2005; 5(3): 213-224.

Davison et al., "Bone Strength: The Whole is Greater Than the Sum of its Parts", Seminars in Arthritis and Rheumatism, vol. 36, No. 1, Aug. 1, 2006, pp. 22-31.

\* cited by examiner

EDIBLE FAT COMPOSITION FOR ENHANCING BONE STRENGTH

This application is a national stage entry of and claims priority to Application Serial No. PCT/IL2008/001053, filed Jul. 31, 2008; and further claims priority to Application Serial No. IL 184982, filed with the Israel Patent Office on Aug. 1, 2007. Both applications to which priority is claimed are herein incorporated by reference for all purposes in their entirety.

FIELD OF THE INVENTION

The invention relates to compositions and methods for increasing bone strength in humans, particularly in a pediatric population, as well as to methods for improving the bone status in humans.

BACKGROUND OF THE INVENTION

All publications mentioned throughout this application are fully incorporated herein by reference, including all references cited therein.

Bone Strength

Traditional Dual X-ray Absorptiometry (DEXA) is a crude expression of bone mineral concentration for a given area. It is limited to measuring one property of the bone only, Bone Mineral Density (BMD), also known as Bone Mass. DEXA does not take into account properties such as bone size or bone architecture. BMD is also influenced by body mass and growth.

Bone strength reflects several varied bone properties and provides a more complete picture of the bone's fragility, as compared to bone density.

Speed of Sound (SOS) is the most appropriate technology to measure bone strength. The propagation of sound waves in bone [Speed of Sound (SOS)] is determined by a number of factors including: mineral density, cortical thickness, elasticity and micro-architecture; thus, possibly providing a more complete picture of bone strength than by measurements of bone density alone.

Bone architecture is defined by the pattern of trabeculae and associated structures. Bone structure is also defined by what is known as "Wolff's law", which determines that: "Every change in the form and function of a bone, or in its function alone, is followed by certain definite changes in its internal architecture and secondary alterations in its external conformation".

General

Osteoporosis is defined by health care professionals today as "a pediatric disease with geriatric consequences". This position has led to a strong focus on the development of healthy bones during infancy, childhood and adolescence, and is expected to contribute to a decrease in the incidence of osteoporosis among tomorrow's adults.

Researchers agree that an individual who does not reach optimal peak bone strength during childhood and adolescence may develop osteoporosis later in life, even if he does not suffer from accelerated bone loss. With many children at risk for less-than-optimal bone development because of limited physical activity, poor nutrition, or other risk factors, the measurement of bone in infancy and childhood is invaluable for ensuring that children develop optimal peak bone strength by adulthood. Special populations at risk for poor bone development include children born prematurely, obese children, and others, who can especially benefit from early assessment of bone development.

A large collection of clinical evidence shows that children's lifestyles can impact in their bone development and affect their skeletal health for years to come. Both lifestyle and nutrition have a significant impact on bone during skeletal development and growth. By the end of adolescence, an adult has accumulated most of the bone that will bring him to maximal peak bone strength. This peak determines the starting point for the decline of bone strength in late adulthood. Along with subsequent bone loss, it will determine a person's risk for osteoporosis later in life.

The impact of all of these lifestyle factors on bone health emphasizes the importance of positive factors improving bone strength or status during these crucial years of infancy and childhood. There is a growing trend among health professionals to urge children and adolescents to adopt an overall healthy lifestyle to help bone reach its maximal strength peak.

Preterm Infants

Despite a steady decline in live birth rates in the United States over the past two decades, the incidence of preterm births (infants born at less than 37 weeks of gestation) is increasing. Metabolic bone disease is a relatively common event in preterm infants because the major period of bone mineral accretion ordinarily occurs during the last trimester of pregnancy, and it is difficult to reproduce in the extra-uterine environment.

Pre-term infants, or premature infants, are classified according to their weight as AGA (appropriate for gestational age) or SGA (small for gestational age). In addition, infants are also classified as LBW (low birth weight, born with less than 2.5 kg), VLBW (very low birth weight, born with less than 1.5 kg), or extreme VLBW (born with less than 1 kg).

Premature infants, especially small (for date) premature infants, are susceptible to metabolic bone disease of prematurity (NIBDP). The degree of osteopenia is inversely related to weight and gestational age. There are data showing that fractures are detected in 10-20% of newborns with a birth weight of less than 1,500 g and gestational age less than 34 weeks. Very low birth weight (VLBW) infants have an increased risk of osteopenia because of limited accretion of bone mass in utero and a greater need for bone nutrients. The prevalence of osteopenia is estimated to be 50% in infants born at extreme low birth (ELBW) with a high fracture rate. Severe morbidity during the neonatal period, development of bronchopulmonary dysplasia, chronic treatment with diuretics and steroids, prolonged immobility and the need for total parenteral nutrition increase the risk of impaired bone health. This emphasizes the essentiality and crucial importance of a high quality and bone strength improving formula.

The rising incidence of preterm births, coupled with their improved survival as a result of highly evolving technologies, has placed an increased need to develop more innovative and cost-effective treatment modalities for preterm infants during the neonatal period and in later life. Pre-term babies do not achieve the bone strength normally accreted during the third trimester of pregnancy, and are often born with low bone strength. Preterm infants, infants born to diabetic mothers, and infants exposed to corticosteroids are considered at risk for compromised bone health.

Most therapeutic efforts to prevent osteopenia of premature infants have focused on nutritional changes in the content of calcium and vitamin D. However, despite the use of mineral-enriched special formulas, these efforts have been only partially successful in improving preterm infants bone mineralization. Again, this may reflect the fact that efforts have focused on quantitative, rather than qualitative changes.

Although prevention of osteopenia is the ultimate goal, identifying infants with existing bone deficiencies would facilitate early interventions such as dietary modifications, exercise programs, or medications.

Bone strength follow up enables tracking of neonate bone. On basis of the results of such tracking, pediatricians/dietitians may recommend quality formulas or other foods for underdeveloped infants/toddlers/children in order to achieve or maintain stronger bones.

Children

Most of the skeletal strength is accrued by the age of 18 years, making bone growth during childhood and adolescence a critical process. Moreover, failure to achieve peak bone strength during this critical period cannot be compensated for later in life. This results in an increased risk of osteopenia and fractures in the future. Pediatricians are in a critical position to affect bone development and prevent behaviors and habits that may lead in the long term to fracture risk and osteoporosis in their patients.

Bone strength and bone development are affected by some important factors that are also important for maintaining bone health. Calcium is one of the main mineral components of bone, supplying density and stiffness to the skeleton, and it is therefore an important factor in maintaining bone health. Recommendations suggest that children and adolescents should increase their calcium intake considerably above present average levels, to ensure adequate development of bone. The diet of many presumably healthy children contains inadequate amounts of dairy products, green vegetables, and other calcium-rich foods. Regular physical activity is another significant factor in bone development. Studies have shown that regular exercise helps strengthen bones. Exercise causes muscles to contract against bone, exerting force on the bone, and strengthening it. Current recommendations include moderate physical activity on most days of the week.

Various other factors are also known to be associated with a negative effect on bone status and the eventual development of osteoporosis. Among these factors are repeated dieting which leads to anorexia nervosa, smoking, alcohol consumption, and intake of carbonated soft drinks. Over-exercising that leads to amenorrhea, a frequent problem of some professional athletes, can also lower bone strength.

Further, children born pre-term or at a low birth weight have low bone strength values for at least six years after birth, indicating an increased risk for weak bones well after infancy. This is probably a result of the high prevalence of Osteopenia of Prematurity in premature infants.

Prior art publications suggested special compositions and methods for increasing bone density and peak bone mass. For example WO05/036978, incorporated herein by reference, discloses an enzymatically prepared fat base composition comprising specific vegetable-derived triglycerides, its preparation and various uses in the field of infant formulas, for preventing calcium and energy losses. US Patent Application No. 2004/0062820 discloses a method for increasing bone mineralization employing a fat blend that is low in palmitic acid.

However, as described above, in order to provide for the development of healthy bones and skeleton, it is important to ensure sufficient bone strength, not only adequate calcium absorption, bone density and bone mass. Bone density, peak bone mass and/or bone mineralization are not always in accord with bone strength, and changing any or all of the first (i.e., bone density, peak bone mass and/or bone mineralization) does not necessarily result in a corresponding change of the latter (bone strength). This notion has been supported by various authors, including Majumdar [Majumdar S. (2003) *Curr. Osteoporos. Rep.* 1(3):105-9], Turner [Turner C. H. (2002) *Osteoporos. Int.* 13(2): 97-104], and Gilsanz [Gilsanz V. (1998) *Eur. J. Radiol.* 26(2):177-82]

Amongst the studies reporting the absence of correlation between bone density and bone mineralization and bone strength, it may be cited for example the study by Takeda and colleagues [Takeda et al. (2004) *J. Amer. Coll. Nutr.* 23(6): 712S-714S] who described the relationship between bone strength and bone mineral concentration in obese rats and concluded that variation in elemental concentrations was not correlated with bone strength. Riggs and colleagues showed that in post-menopausal women, fluoride treatment increased bone mass and concomitantly increased skeletal fragility, particularly of non-vertebral bones [Riggs et al. (1990) *N. Engl. J. Med.* 322(12):802-9]. Divittorio et al. reached a similar conclusion [Divittorio et al. (2006) *Pharmacotherapy* 26(1):104-14]. In contrast, raloxifene, a selective estrogen receptor modulator, significantly improved vertebral bone strength independent of bone mineral density [Allen et al. (2006) *Bone* 39:1130-1135].

Increase in bone strength reflects lower liability to fractures and other mechanical bone defects.

It is therefore an object of the present invention to provide compositions and methods for increasing and maintaining bone strength in newborns, infants, toddlers, children and adolescents.

It is a further object of the invention to provide compositions and methods for improving and maintaining bone status in humans.

SUMMARY OF THE INVENTION

Thus in a first aspect, the present invention provides a method of increasing bone strength and/or increasing bone resistance to bending and/or improving bone architecture and/or maintaining bone status in a human, comprising administering to said human a composition comprising a fat source, wherein said fat source is a triglyceride fat source comprising triglycerides with 15-55% palmitic acid moieties out of the total fatty acids and the level of palmitic acid moieties at the sn-2 position of the glycerol backbone is at least 30% (w/w) of total palmitic acid.

Particularly, said fat source is characterized by having the following parameters: (i) at least 30%, preferably 33%, more preferably 40% of the total palmitic acid residues are at the sn-2 position of the glycerol backbone; (ii) at least 50%, preferably 70% of the fatty acid moieties at the sn-1 and sn-3 positions of the glycerol backbone are unsaturated; (iii) at least 35%, preferably at least 40%, of said unsaturated fatty acid moieties at the sn-1 and sn-3 positions are oleic acid moieties; and (iv) at least 4%, preferably at least 6%, of said unsaturated fatty acid moieties at the sn-1 and sn-3 positions are linoleic acid moieties.

In one embodiment of said method of the invention, said human is a newborn, an infant, a toddler, a child or an adolescent.

In another embodiment of said method of the invention, said composition comprises a fat source as defined above blended with a mixture of vegetable oils, wherein said mixture comprises oils selected from the group consisting of, but not limited to, soy, palm tree, canola, coconut, palm kernel, sunflower, corn and rapeseed oil.

In a further embodiment of said method of the invention, said human is at risk of impaired bone strength.

In a further embodiment of the invention, said fat source is comprised in any one of food article and infant formula, wherein said food article is selected from bakery products, including bread, particularly biscuits and pastries, dairy products, including milk and dairy drinks, ice cream, cereal products, sauces, spreads, including margarine, oils and fats, soy products, meat products, fried food products, confectionery products, candy bars, candies and chocolates, snacks, drinks and shakes, instant drink products, prepared foods for infants and young children, including prepared cooked mashed vegetables and/or fruits, condiment products, and cooking oils and fats.

In an even further embodiment of said method of the invention, said infant formula comprises said fat source, together with a protein source, a carbohydrate source, minerals, vitamins and optionally at least one of carrier, diluent, additive or excipient.

In another aspect the present invention provides an edible fat source for use in increasing bone strength and/or increased bone resistance to bending and/or improving bone architecture and/or maintaining bone status in a human, wherein said fat source is a triglyceride fat source comprising triglycerides with 15-55% palmitic acid moieties out of the total fatty acids and the level of palmitic acid moieties at the sn-2 position of the glycerol backbone is at least 30% (w/w) of total palmitic acid.

In particular, said fat source is characterized by having: (i) at least 30%, preferably 33%, more preferably 40% of the total palmitic acid residues are at the sn-2 position of the glycerol backbone; (ii) at least 50%, preferably 70% of the fatty acid moieties at the sn-1 and sn-3 positions of the glycerol backbone are unsaturated; (iii) at least 35%, preferably at least 40%, of said unsaturated fatty acid moieties at the sn-1 and sn-3 positions are oleic acid moieties; and (iv) at least 4%, preferably at least 6%, of said unsaturated fatty acid moieties at the sn-1 and sn-3 positions are linoleic acid moieties.

In one embodiment of said fat source, said human is a newborn, an infant, a toddler, a child or an adolescent.

In another embodiment of said fat source of the invention, said human is at risk for impaired bone strength.

In a further aspect the present invention provides a food article, wherein said food article comprises the fat source as described in the invention, and it is a food article for increasing bone strength and/or maintaining bone status in a human, wherein said food article is selected from bakery products, including bread, particularly biscuits and pastries, dairy products, including milk and dairy drinks, ice cream, cereal products, sauces, spreads, including margarine, oils and fats, soy products, meat products, fried food products, confectionery products, candy bars, candies and chocolates, snacks, drinks and shakes, instant drink products, prepared foods for infants and young children and for adults, including prepared cooked mashed vegetables and/or fruits, condiment products, and cooking oils and fats.

In one preferred embodiment, said food article is for maintaining and/or increasing bone strength, wherein said human is a newborn, an infant, a toddler, a child or an adolescent, particularly when said human is at risk for impaired bone strength.

Lastly, the present invention provides a commercial package comprising:

(a) a fat source which upon enteral administration to a human it increases bone strength;

(b) optionally at least one of edible physiologically acceptable protein, carbohydrate, vitamin, mineral and active or non-active additive;

(c) optionally at least one edible physiologically acceptable carrier or diluent for carrying the constituent/s defined in a) and b);

(d) means and receptacles for admixing the constituents defined in a), b) and/or c); and (e) instructions for use.

In one preferred embodiment of the commercial package of the invention, said fat source is a triglyceride fat source comprising triglycerides with 15-55% palmitic acid moieties out of the total fatty acids and the level of palmitic acid moieties at the sn-2 position of the glycerol backbone is at least 30% (w/w) of total palmitic acid.

In particular, said fat source is characterized by: (i) at least 30%, preferably 33%, more preferably 40% of the total palmitic acid residues are at the sn-2 position of the glycerol backbone; (ii) at least 50%, preferably 70% of the fatty acid moieties at the sn-1 and sn-3 positions of the glycerol backbone are unsaturated; (iii) at least 35%, preferably at least 40%, of said unsaturated fatty acid moieties at the sn-1 and sn-3 positions are oleic acid moieties; and (iv) at least 4%, preferably at least 6%, of said unsaturated fatty acid moieties at the sn-1 and sn-3 positions are linoleic acid moieties.

Histogram representing the measurement of ultimate stiffness in rats fed three diets. Rats fed Diet A show superior resistance to bending, represented in the figure as ultimate stiffness (u.s.). Apparent differences seen between rats group fed with diet A (H2P) and with diet B (HP) ($p=0.004$) or with diet C (LP) ($p=0.038$) may be due to an increased rate of bone mineral apposition. A, B, and C represent diet A, diet B and diet C, respectively.

Figure 1:
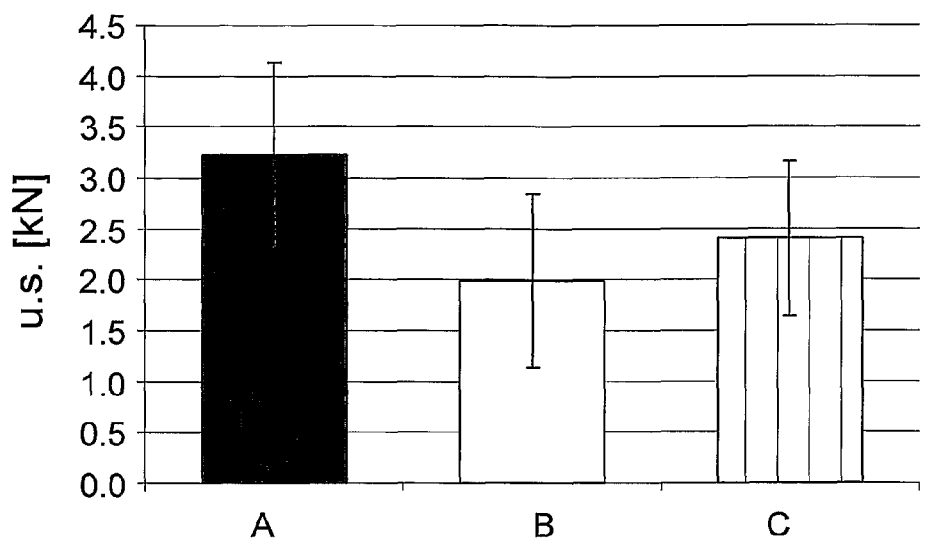
FIG. 1: Ultimate stiffness parameter measurement with maximum load.
Figure 2:
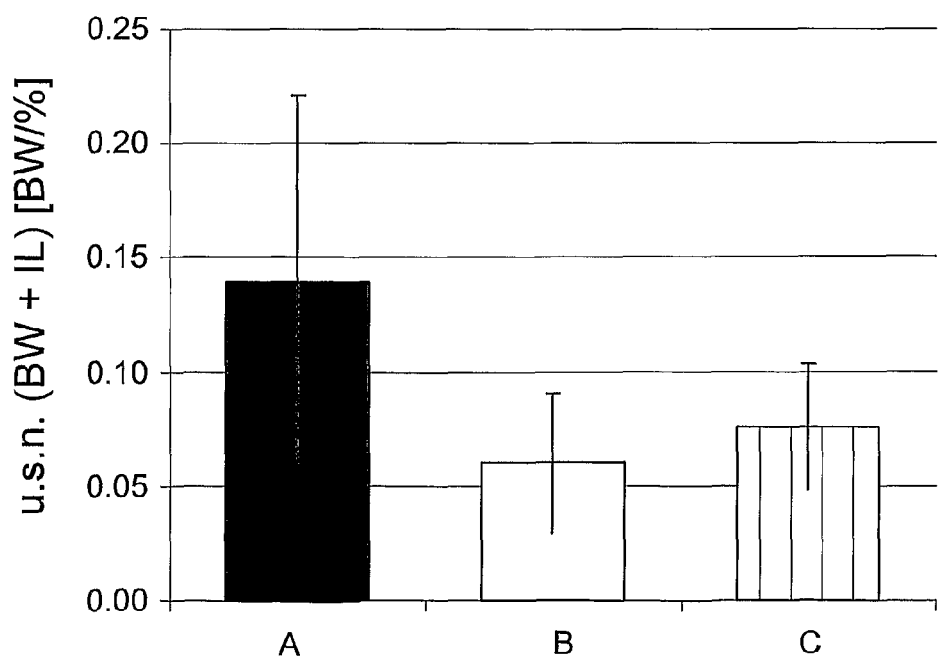

FIG. 2: Histogram representing normalization of stiffness (u.s.n.) to body mass and vertebrae height in rats fed three diets.

Normalization of stiffness (u.s.n.) to body mass and vertebrae height yields significant differences between structural stiffness of rats fed diets A, B ($p=0.007$) and C ($0.031$). A, B, and C represent diet A, diet B and diet C, respectively.

DETAILED DESCRIPTION OF THE INVENTION

In search for a composition for increasing bone strength and/or improving bone status and/or improving bone architecture in newborns, infants, toddlers, children, adolescents or adults, the present inventors have found that an edible composition of matter comprising a suitable fat source, particularly a triglyceride composition that is rich in palmitic acid residues, can achieve these required objects.

As understood herein, bone status refers to bone health, and it is dependent on the age and gender of the subject, but generally includes bone mineral content, bone mineral density, structural stiffness, bone microarchitecture, elasticity, cortical thickness, etc.

Thus the composition of the invention (InFat, in the form of concentrate base or blend) is particularly useful in maintaining and/or increasing bone strength in humans suffering or prone to reduced bone strength.

Bone strength is usually defined as the amount of loading force required to cause the material to fail under a certain loading condition [Turner & Burr (1993) *Bone* 14:595-608; Currey & Butler (1975) *J Bone Joint Surg Am* 57:810-814]. A further definition of bone strength, as presented by Petit and colleagues, refers to strength as "the load necessary to cause material yield" [Petit et al. (2005) *J Musculoskelet Neuronal Interact* 5(3):213-224]. This further definition takes into consideration the parameters evaluated in a test of bone material strength, when done with a small rod-shaped piece of bone that is gradually pulled on its ends causing it to stretch in length. Up to a certain point, the bone can sustain stress (force) without much strain (deformation). Thus, the bone may be stretched to a certain point and elastically return to its original length. This property is also defined as the elastic modulus (or Young's modulus), and it is also referred to as "material stiffness". Beyond such point, damage occurs and the material begins to yield, so that when released it does not return completely to its original length. Ultimately, the material fails to yield, and at that point, fracture occurs [Petit (2005) id ibid.].

Other bone strength parameters, particularly those obtained through measurements using ultrasound bone sonometer, particularly quantitative ultrasound, using axial transmission technology, are mineral density, elasticity, cortical thickness, and microstructure.

Biomechanical properties of vertebral body specimens may be analyzed in materials testing machines, which provide load and deformation values. These are usually only done in animal models, since it is necessary to collect the specimen (the bone) in order to perform the analysis. Load-deformation curves provide parameters for calculating strain at ultimate load, ultimate load, ultimate stiffness, and energy absorption at ultimate load. These parameters reflect the strength of the vertebral body.

Bone mass density is a measure of bone density. Bone density is the amount of bone tissue in a certain volume of bone. It can be measured using quantitative computed tomogram.

The inventors have shown, particularly with the results presented in Example 4, that a modified diet comprising an InFat blend described in the invention, induced increased bone strength in treated rats as compared to rats fed with a control diet.

Thus, it was surprisingly found by the inventors that animals fed with a diet rich in palmitic acid at the sn-2 position showed increased bone strength, as measured through axial transmission technology.

Thus, the composition of the invention is also particularly suitable for treatment of premature infants, especially small premature infants, that are susceptible to bone diseases and defects, for example metabolic bone disease of prematurity (MBDP); infants with very low birth weight (VLBW), particularly those with increased risk of osteopenia; infants born at extreme low birth weight (ELBW) with a high fracture rate; neonates with bronchopulmonary dysplasia; neonates under chronic treatment with diuretics and steroids or exposed to steroids; infants born to diabetic mothers; and others. Subjects affected by any of these conditions are at risk of impaired bone strength.

Osteopenia is a decrease in bone mineral density that can be a precursor condition to osteoporosis. A diagnosis of osteopenia reflects bone mineral density (BMD) which is lower than normal peak BMD but not low enough to be classified as osteoporosis.

Thus, the present invention has as a goal to provide a method of increasing bone strength and/or increasing bone resistance to bending and/or improving bone architecture and/or maintaining bone status in a human, comprising administering to said human a composition comprising a fat source which is rich in palmitic acid, wherein said fat source is a triglyceride fat source in which the level of palmitic acid moieties at the sn-2 position of the glycerol backbone is at least 30% (w/w) of total palmitic acid, and the total palmitic acid content is 15-55% of the total fatty acids.

In a particular embodiment of the invention the fat source comprises triglycerides with 15-55% C16:0 fatty acids of the total fatty acids.

Thus, the palmitic acid content of said fat source may be 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54% or 55% of the total fatty acids.

The essential features of the concentrate fat base composition are: (i) at least 30%, preferably 33%, more preferably 40% of the total palmitic acid residues at the sn-2 position of the glycerol backbone; (ii) at least 50%, preferably 70% of the fatty acid moieties at the sn-1 and sn-3 positions of the glycerol backbone being unsaturated; (iii) at least 35%, preferably at least 40%, of said unsaturated fatty acid moieties at the sn-1 and sn-3 positions being oleic acid moieties; and (iv) at least 4%, preferably at least 6%, of said unsaturated fatty acid moieties at the sn-1 and sn-3 positions being linoleic acid moieties.

More specifically, the fat source comprises 0-20% C12:0 fatty acids of the total fatty acids, preferably 5-15%; 0-15% C14:0 fatty acids of the total fatty acids, preferably 2-10%; 15-55% C16:0 fatty acids of the total fatty acids, of which over 30% are esterified at the sn-2 position of the glycerol backbone; 1-7% C18:0 fatty acids of the total fatty acids, preferably 2-5%; 25-75% C18:1 fatty acids of the total fatty acids, preferably 28-45%; 2-40% C18:2 fatty acids of the total fatty acids, preferably 5-20%; 0-8% C18:3 fatty acids of the total fatty acids, preferably 1-3%; other fatty acids are each present in levels of less than 8% of the total fatty acids, preferably less than 5%.

Specific fat sources are described in WO05/036987. These include fat concentrates (fat bases), fat blends, infant formulas comprising the concentrates/blends and other foods and food articles.

Of particular interest are fat sources which are based on synthetic oil (which can be produced both chemically and, preferably, enzymatically) which mimics the triglyceride composition of human breast milk fat. This oil has, preferably, a high level of palmitic acid at the sn-2 position of the triglycerides, and a high level of unsaturated fatty acids at sn-1 and sn-3 positions. This ingredient is also referred to herein as InFat™ (Enzymotec Ltd., Migdal HaEmeq, Israel), and it is defined in Table 1A.

More specifically, the fat source used by the present invention may be a concentrate, particularly an enzymatically prepared fat base composition comprising a mixture of vegetable-derived triglycerides, with a total palmitic acid residues content of at most 38% of the total fatty acid residues; and with at least 60% of the fatty acid moieties at the sn-2 position of the glycerol backbone being palmitic acid residues.

InFat is an advanced fat-base ingredient for the production of fat preparations used in infant nutrition and in infant formulas. It is an exclusive fat base, designed and manufactured with a specific triglyceride composition and structure, which has now been found to be efficient in increasing bone strength, particularly in infant populations prone to problems in bone development, as well as other such populations.

In one preferred embodiment, said fat source comprises triglycerides with 0-20% C12:0 fatty acids of the total fatty acids, preferably 5-15%; 0-15% C14:0 fatty acids of the total fatty acids, preferably 2-10%; 15-55% C16:0 fatty acids of the total fatty acids, of which over 30% are esterified at the sn-2 position of the glycerol backbone; 1-7% C18:0 fatty acids of the total fatty acids, preferably 2-5%; 25-75% C18:1 fatty acids of the total fatty acids, preferably 28-45%; 2-40% C18:2 fatty acids of the total fatty acids, preferably 5-20%; 0-8% C18:3 fatty acids of the total fatty acids, preferably 1-3%; other fatty acids are each present in levels of less than 8% of the total fatty acids, preferably less than 5%.

Thus, the fat source may comprise: 0%, 1%, 2%, 3%, 4%, 5%, 6%, 7%, 8%, 9%, 10%, 11%, 12%, 13%, 14%, 15%, 16%, 17%, 18%, 19%, or 20% of C12:0 fatty acids of the total fatty acids; 0%, 1%, 2%, 3%, 4%, 5%, 6%, 7%, 8%, 9%, 10%, 11%, 12%, 13%, 14% or 15% C14:0 fatty acids of the total fatty acids; 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54% or 55% C16:0 fatty acids of the total fatty acids; 1%, 1.2%, 1.4%, 1.6%, 1.8%, 2%, 2.2%, 2.4%, 2.6%, 2.8%, 3%, 3.2%, 3.4%, 3.6%, 3.8%, 4%, 4.2%, 4.4%, 4.6%, 4.8%, 5%, 5.2%, 5.4%, 5.6%, 5.8%, 6%, 6.2%, 6.4%, 6.6%, 6.8%, or 7% C18:0 fatty acids of the total fatty acids; 25%, 27%, 28%, 30%, 32%, 33%, 35%, 37%, 39%, 40%, 42%, 43%, 44%, 45%, 47%, 49%, 50%, 52%, 53%, 55%, 57%, 59%, 60%, 62%, 63%, 65%, 67%, 69%, 70%, 72%, 74% or 75% C18:1 fatty acids of the total fatty acids; 2%, 4%, 5%, 6%, 7%, 8%, 9%, 10%, 11%, 12%, 13%, 14%, 15%, 16%, 17%, 18%, 19%, 20%, 22%, 23%, 25%, 27%, 28%, 30%, 32%, 33%, 35%, 37%, 39%, 40% C18:2 fatty acids of the total fatty acids; 0%, 0.5%, 1%, 1.2%, 1.4%, 1.6%, 1.8%, 2%, 2.2%, 2.4%, 2.6%, 2.8%, 3%, 3.2%, 3.4%, 3.6%, 3.8%, 4%, 4.2%, 4.4%, 4.6%, 4.8%, 5%, 5.2%, 5.4%, 5.6%, 5.8%, 6%, 6.2%, 6.4%, 6.6%, 6.8%, 7%, 7.2%, 7.5%, 7.8% or 8% C18:3 fatty acids of the total fatty acids.

The fat source used by the present invention can also be a substitute human milk fat composition comprising a blend of at least 25% of the said fat base with up to 75% of at least one vegetable oil. The following Examples present eight blends, InFat 1, InFat 2, InFat 3, InFat 4, InFat 5, InFat 6, InFat 7 and InFat 8 wherein different amounts of the fat base concentrate (InFat) were used, from 30% up to 83% of the content of the blend.

The vegetable oil used in the preparation of blends may be at least one of soy, palm tree, canola, coconut, palm kernel, sunflower, corn and rapeseed oil, as well as other vegetable oils and fats and mixtures thereof.

Most importantly, the fat source of the present invention may be used in the preparation of infant formula. The infant formula used by the invention comprises in addition to said fat source at least one protein component and optionally at least one of carbohydrate source, vitamins, minerals, nucleotides and amino acids.

The terms "lipid" and "fat" are used herein synonymously.

In addition to being comprised in an infant formula, the fat source used by the invention may be comprised in a food article such as, but not limited to bakery products, including bread, particularly biscuits and pastries, dairy products, including milk and dairy drinks, ice cream, cereal products, sauces, spreads, including margarine, oils and fats, soy products, meat products, fried food products, confectionery products, candy bars, candies and chocolates, snacks, drinks and shakes, instant drink products, prepared foods for infants and young children and for adults, including prepared cooked mashed vegetables and/or fruits, condiment products, and cooking oils and fats.

The method of the invention is effected through administering, to a subject in need, an infant formula or a food article prepared with and comprising the fat source as described in the invention, either in the form of a concentrate base or in the form of a blend. Non-limiting examples of a concentrate base are InFat A, B, C or D, and non-limiting examples of a blend are InFat 1, 2, 3, 4, 5, 6, 7 or 8.

Administration is usually via oral or enteral, which may include the use of gavage feeding, with a gastric feeding tube, sonda, etc, particularly where adapted for infant feeding.

The present invention further provides the use of a fat source which is rich in palmitic acid, as described in the invention, wherein said fat source is a triglyceride fat source in which the level of palmitic acid moieties at the sn-2 position of the glycerol backbone is at least 30% (w/w) of total palmitic acid, and the total palmitic acid content is 15-55% of the total fatty acids, in the preparation of a composition for increasing bone strength and/or increasing bone resistance to bending and/or improving bone architecture and/or maintaining bone status in a human.

Such composition is preferably to be administered via oral or enteral, to subjects at risk of impaired bone strength.

In a further aspect, the invention relates to a commercial package for preparing an edible fat source or food article which is recommended for increasing bone strength and/or increasing bone resistance to bending and/or improving bone architecture and/or maintaining bone status in a human, in accordance with the invention. In addition to the active and non-active constituents, the commercial package contains instructions for use. These include terms of storage, instructions for preparation of the fat source or food article for administration, required dilutions, dosages, frequency of administration and the like. A commercial package in accordance with the invention may also contain the fat source in a ready-to-use form, together with instructions for use. Dosages are usually determined according to age, weight, sex and condition of the subject, in accordance to good medical practice known to the attending physician and other medical personnel.

The present invention is defined by the claims, the contents of which are to be read as included within the disclosure of the specification.

Disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following Examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Example 1

Composition of InFat and InFat Blends

The following Table 1A details the contents of a fat source preferably used by the invention (InFat, also referred to as "the concentrate material") and of eight InFat blends which are also suitable for use as the fat source in the methods and compositions of the invention. The preparation of these fat sources is described in said WO05/036987.

TABLE 1A

InFat - the concentrate base

| Fatty acid | InFat A | InFat B | InFat C | InFat D |
|---|---|---|---|---|
| C16 | 32 | 29 | 27.6 | 33 |
| Sn-2 C16 | 67.2 | 53.9 | 54.8 | 52.9 |
| ratio | 70.0 | 62 | 66.2 | 53.5 |
| C18 | 4 | 2.6 | 2.6 | 3 |
| C18:1 | 53.1 | 55.5 | 55.4 | 52 |
| C18:2 | 8 | 9 | 9.6 | 10 |

TABLE 1B

The InFat blends

| Content | InFat 1 | 2 | 3 | 4 | 5 | 6 | 7 | 8 |
|---|---|---|---|---|---|---|---|---|
| Fatty acid (%) | | | | | | | | |
| C12 | 11.1 | 7.2 | 7.8 | 6.5 | 4.4 | 8.14 | 8.1 | 10.1 |
| C14 | 4.5 | 3.1 | 3.3 | 2.8 | 2.1 | 2.94 | 2.8 | 3.7 |
| C16 | 22.8 | 25.4 | 26.9 | 25.1 | 27.7 | 21.60 | 20.9 | 22.1 |
| Sn-2 C16 | 33.4 | 42.9 | 48.9 | 50.8 | 56.9 | 31.3 | 31.16 | 28.7 |
| ratio | 48.7 | 56.3 | 60.7 | 67.4 | 68.5 | 48.31 | 50.4 | 43.3 |
| C16:1 | | | | | | | | |
| C18 | 2.3 | 3.0 | 3.1 | 3.5 | 4.0 | 2.65 | 2.6 | 2.7 |
| C18:1 | 38.4 | 40.8 | 41.6 | 47.9 | 46.6 | 42.71 | 45.1 | 43.9 |
| C18:2 | 13.5 | 15.6 | 12.8 | 8.6 | 11.7 | 17.96 | 16.8 | 13.6 |
| C18:3 | 1.7 | 0.6 | | 1.4 | | 1.69 | 1.7 | 1.4 |
| % InFat A | 30 | 50 | 63 | 73 | 83 | | | |
| % InFat B | | | | | | 60 | | |
| % InFat C | | | | | | | 60 | |
| % InFat D | | | | | | | | 52 |
| % Coconut oil | 23 | 15 | 16 | 13.5 | 9.3 | | | 21 |
| % Palm Kernel Oil | | | | | | 18 | 18 | |
| % Palm oil | 21 | 15 | 9 | | | | | |
| % Sunflower | | 5 | | | 7.7 | | | |
| % Corn oil | 10 | 10 | 12 | | | | | 11 |
| % Rapeseed | 16 | 5 | | 13.5 | | 4 | 4 | 16 |
| % Soybean | | | | | | 18 | 18 | |
| % Total | 100 | 100 | 100 | 100 | 100 | | | |

C16 represents the total palmitic acid content. Sn-2 C16 represents the percentage palmitic acid of total sn-2 position fatty acids. The ratio means the percentage of sn-2 palmitic acid of total palmitic acid normalized per position, as per the formula {(% of sn-2 palmitic)/(3×% total palmitic acid)}× 100. All numbers represent % (w/w), except for the ratio, which is defined as %.

Example 2

Infant Formula Based on InFat

An infant formula comprising InFat and additional oils and fats that mimic the human breast milk fat composition is prepared as follows: a selected formulation (e.g. one of those of Table 1A) is blended/mixed with a suitable vegetable oil, or a mixture of vegetable oils. The resulting lipid mixture is the lipid ingredient, which is mixed together with the other components (proteins, carbohydrates, minerals, vitamins and others) which result in the infant formula. The slurry is passed through a pressure homogenizer to get a stable emulsion. Homogenized product is then dried in a spray drier to obtain the final product. Other additives may be added to the dry powder to obtain final formulation, for example prebiotics and/or probiotics (like LGG, BB12, GOS/FOS).

The fat fraction produced by the blending of InFat with other oils and fats as described above is further blended with other nutrients such as proteins, minerals, vitamins and carbohydrates to yield a food product supplying the infant with the major nutrients also found in human milk. The nutrients and fats are homogenized using pressure homogenization and spray dried to yield a homogenous powder. The powder is further re-dispersed in water (approximately 9 g powder per 60 ml water) to yield a ready-to-feed formula. The fat content of the ready feed is approximately 3.5 g per 100 ml which corresponds to the fat content of human breast milk, which is in the range of 30-40 g/L.

An exemplary fatty acid composition of a blend of InFat A (30%) with other oils and fats used to create an infant formula is presented in Table 2 and the details of ingredients and properties of the formula are defined in Table 3 below.

TABLE 2

Fatty acid composition of a blend of InFat

| Fatty acid | % |
|---|---|
| C10:0 | 1.3 |
| C12:0 | 10.3 |
| C14:0 | 4.3 |
| C16:0 | 23.5 |
| sn-2 C16:0 (% of total C16:0) | 43 |
| C18:0 | 3.2 |
| C18:1 | 39.2 |
| C18:2 | 13.6 |
| C18:3 | 1.7 |
| C20:0 | 0.3 |
| C20:1 | 0.3 |
| C22:0 | 0.2 |

TABLE 3

Ingredients and properties of a formula prepared with a blend of InFat

| | per 100 g powder | Per 100 ml ready to feed |
|---|---|---|
| Energy (kcal) | 508 | 68 |
| Sodium (mg) | 140 | 18.8 |
| Protein (g) | 11.4 | 1.5 |
| Lacatalbumin/Casein (60/40) | | |
| Fat (g) | 26.5 | 3.5 |
| Saturated fat (g) | 11.3 | 1.49 |
| Linoleic acid (mg) | 5000 | 670 |
| Alpha-linolenic acid (mg) | 530 | 71 |
| Arachidonic acid (mg) | 115 | 15.3 |
| Docosahexaenoic acid (mg) | 108 | 14.4 |
| Cholesterol (mg) | 2 | 0.3 |
| Lactose (g) | 56 | 7.5 |
| Calcium (mg) | 430 | 57.3 |
| Phosphorus (mg) | 250 | 33.5 |
| Potassium (mg) | 420 | 56.3 |
| Chloride (mg) | 300 | 40.2 |
| Iron (mg) | 5.25 | 0.7 |
| Magnesium (mg) | 50 | 6.7 |
| Zinc (mg) | 3.5 | 0.47 |
| Copper (mcg) | 300 | 40.2 |
| Manganese (mcg) | 45 | 6 |
| Iodine (mcg) | 45 | 6 |
| Taurine (mg) | 45 | 6 |
| Vitamin A (I.U.) | 1500 | 200 |
| Vitamin D (I.U.) | 300 | 40.2 |
| Vitamin E (mg) | 10 | 1.3 |

TABLE 3-continued

Ingredients and properties of a formula prepared with a blend of InFat

|  | per 100 g powder | Per 100 ml ready to feed |
|---|---|---|
| Vitamin K (mcg) | 45 | 6 |
| Vitamin C (mg) | 60 | 8 |
| Vitamin $B_1$ (mcg) | 400 | 53 |
| Vitamin $B_2$ (mcg) | 800 | 127 |
| Vitamin $B_6$ (mcg) | 375 | 50 |
| Vitamin $B_{12}$ (mcg) | 1.15 | 0.2 |
| Niacin (mg) | 6 | 0.8 |
| Panthothenic acid (mg) | 3 | 0.4 |
| Folic acid (mcg) | 67 | 9 |
| Biotin (mcg) | 14.3 | 1.9 |
| Choline (mg) | 37.5 | 5 |
| Inositol (mg) | 22.5 | 3 |
| Moisture (%) | 3 | |

The level of fat and the exact composition can be adapted in order to yield infant formulas designed to mimic the different lactation periods.

Example 3

Biscuits and Pastry Based on InFat

A biscuit or pastry product designed nutritionally for infants and young children, having several percentages of oils and fats, all or most being InFat. Such product may include 1 to 15% fat or oil, preferably 3 to 9%.

In a specific recipe, biscuits were produced from dough comprising the following ingredients: Wheat flour (41%), Cane sugar (20.5%), Water (25.8%), InFat (8.2%), Corn starch (2.9%), and Leavening agent (1.6%). Another recipe includes Wheat flour (42.2%), Cane sugar (21.1%), Water (16.8%), InFat (8.4%), Corn starch (11.0%), Leavening agent (0.3%), and Salt (0.2%).

Example 4

The Effects of Infant Diet Based on InFat 6 Blend (InFat 6), on Bone Strength in Rats The efficacy of InFat blend 6 was investigated in an animal model study. The study evaluated bone mineralization and bone strength in animals fed with diet enriched with palmitic acid at the sn-2 position (InFat 6 blend) compared to animals fed with a diet enriched with palmitic acid at the sn-1 and sn-3 position.

A series of tests were performed to characterize the biomechanical properties of vertebral bodies in weanling rats undergoing controlled feeding regimes that employed advanced lipid chemistry schemes intended to alter (increase) rates of bone formation.

Study Design:

48 Male Sprague-Dawley rats were obtained from the Harlan Laboratories (Rehovot, Israel) at 21 days of age, immediately after weaning and at body weight of 40-50 g.

The rats were randomly assigned to receive three different diets, for 2 weeks period of feeding (12 animals per group). The diets supplied were different in their fat content:

1. Diet A: Diet with oil containing high palmitic acid at sn-2 position
2. Diet B: Diet with oil containing high palmitic acid at sn-1 and sn-3 position
3. Diet C: Diet with oil containing low palmitic acid At the end of the experiment (feeding day 15) animals were anesthetized, sacrificed and cadavers were frozen at −80° C. until the day of performing the bone strength tests.

Diets

The standard rat chow, Teklad Global 18% Protein Rodent Diet manufactured by Harlan Tekled Ltd, USA (cat #2018) was used as control diet. Custom-made rat diets were manufactured by Harlan Tekled Ltd; USA. All custom-made diets were similar with respect to nutrient content and differ only in respect to the type of oil (Table 5).

TABLE 4

Fatty acids composition of supplemented oils (% of total fatty acids)

| Fatty acid (% from total FA) | InFat 6 | Preparation control I | Preparation control II |
|---|---|---|---|
| C8 | 0.59 | 0.62 | 0.97 |
| C10 | 0.74 | 0.58 | 0.94 |
| C12 | 8.14 | 8.23 | 13.16 |
| C14 | 2.94 | 3.34 | 4.60 |
| C16 | 21.60 | 22.59 | 8.19 |
| C16 sn-2 ratio | 48.31 | 13.38 | 11.40 |
| C18 | 2.65 | 3.55 | 2.71 |
| C18:1 | 42.71 | 41.90 | 47.31 |
| C18:2 | 17.96 | 16.40 | 18.77 |
| C18:3 | 1.69 | 1.69 | 1.93 |
| others | 0.90 | 4.63 | 1.37 |

TABLE 5

Diet Compositions (% by weight)

|  | Diet A | Diet B | Diet C |
|---|---|---|---|
| Protein | 19.1 | 19.1 | 19.1 |
| Carbohydrate | 61.9 | 61.9 | 61.9 |
| Fat | 6.2 | 6.2 | 6.2 |
| Calories (kcal/gr) | 3.8 | 3.8 | 3.8 |
| InFat 6 (g/kg) | 60 | | |
| Preparation control I (g/kg) | | 60 | |
| Preparation control II (g/kg) | | | 60 |

Bone Strength Analysis

A series of tests were performed to characterize the biomechanical properties of vertebral bodies in weanling rats.

The biomechanical characterization encompassed sensitive functional measurements of the mechanical competency of trabecular bone by uniaxial compression of the $5^{th}$ lumbar vertebral body. All tests were performed with a universal testing machine (Zwick 1456, Ulm Germany) and custom fixtures specifically constructed for the study application. Bone stiffness was calculated from the linear portion of the load and displacement curve load-deformation curve of the tested bone.

Bone strength measurements were performed using Omnipath®, Sunlight Omnisense's axial transmission technology, also known as A-QUS (axial quantitative ultrasound).

Results

Bone Strength Measurements:

Structural stiffness was significantly higher in the diet A group (high palmitic acid at sn-2 position diet) compared to diet B group (high palmitic acid at sn-1 and sn-3 position diet) (p=0.004) and significantly higher compared to diet C group (low palmitic oil diet) (p=0.038) as shown in FIG. 2. Normalization of stiffness to body mass and vertebrae height yielded significant differences as well between diet A and diet B or diet C (p=0.007, 0.031, respectively) in structural stiffness (FIG. 3), which provided bone resistance to breaking. The elastic modulus, the ultimate stiffness per mm2, reflects the capability of the bone tissue to withstand bending.

TABLE 6

Biomechanical Analysis of Rat Vertebrae L5

| Biomechanical data | Diet A | Diet B | Diet C |
|---|---|---|---|
| Number of samples | 11 | 11 | 10 |
| Body weight [g] | 107.7 ± 4.2 | 106.6 ± 8.0 | 113.4 ± 5.3 |
| Pre-load [N] | 2 | 2 | 2 |
| Deformation rate [mm/s] | 0.1 | 0.1 | 0.1 |
| Ultimative stiffness [kN] | 3.2 ± 0.9 | 2.0 ± 0.9 | 2.4 ± 0.8 |
| Ultimate stiffness Normalized (BW** + IL***) [BW**/%] | 0.14 ± 0.08 | 0.06 ± 0.03 | 0.075 ± 0.03 |

In conclusion, mechanical competency of rat weanling bone appears to be sensitive to the applied dietary intervention. Specifically, the higher structural stiffness in rats fed with Diet A group would point to an accelerated rate of bone structural strength.

Example 5

Effects of InFat 7 on Bone Strength in Formula-Fed Term Chinese Infants: a Double-Blind, Randomized, Placebo-Controlled Trial Efficacy of InFat Blend 7

The efficacy of InFat blend 7 (InFat 7) is investigated by a double-blind, randomized, placebo-controlled, 6-month duration trial in term Chinese infants. The study demonstrates the effect of formula having high proportion of palmitate at the sn-2 position (the invention, InFat™ 7 from the InFat blends listed on Table 1B), compared to standard vegetable oil based formula, on bone strength outcomes in Chinese term infants.

The purpose of this study is to assess the bones strength in infants by measuring the speed of sound (SOS) of an ultrasound wave along the bone. The Speed of Sound (SOS) measurements are being done by quantitative ultrasound technology, Sunlight Omnisense® 7000P (Omnisense 7000P), a product of SunLight company (Sunlight Medical Inc., Somerset, N.J.). Omnisense 7000P is an ultrasound-based diagnostic device developed especially to assess bone strength in the pediatric population. Clinical studies have shown that the device is capable of detecting changes in bone strength that result from excess body weight and calcium consumption levels Sunlight has developed a number of reference databases for bone assessment of the pediatric population, based on gender and ethnic origin. The currently available databases are male and female databases which includes the Chinese population as well. Sunlight Medical's new pediatric Chinese reference database, collected in urban areas in China, has enhanced the applicability of Sunlight Omnisense® 7000P for pediatric Chinese populations worldwide.

Study Design:

Following screening, 80 infants are randomized to one of two treatment groups, 40 infants in each treatment group:
1. Formula A: Formula containing InFat blend 7 (Table 7).
2. Formula B: Control formula containing standard vegetable oil (Table 7).

TABLE 7

Fatty acid composition (% of weight of total fatty acids)

| Fatty acid | Formula A (InFat) | Formula B (control) |
|---|---|---|
| C12:0 | 9 | 9 |
| C14:0 | 3 | 3 |
| C16:0 | 21 | 21 |
| C16:0 at sn-2 position | 49 | 10 |
| C18:0 | 2.5 | 2.5 |
| C18:1 | 43 | 43 |
| C18:2 | 16 | 16 |
| C18:3 | 1.5 | 1.5 |

Eligible infants are enrolled in the study within 8-10 days after birth. Infants are randomized to one of two groups: treatment group (formula A) or control (formula B). Both groups receive the formula for 6 months and their bone strength is measured at baseline and during the study after 6 and 12 weeks.

Methods:

QUS (Quantitative Ultrasound) Measurements of Tibial Bone SOS:

SOS measurements of midshaft tibia are taken using Sunlight Omnisense® 7000P QUS.

Results

The expected results are that bone SOS measured using quantitative ultrasound technology in infants fed with formula A (InFat 7 blend) are significantly higher than SOS measured in infants fed with formula B (control formula) following 6 weeks and 12 weeks of feeding. Bone SOS measurements of infants fed with formula A are increased with time in more significant pace compared to infants fed with formula B. Such results will likely indicate that the addition of palmitic acid at sn-2 position to infant formula results will be significantly higher whole body bone mass compared to formula B.

Example 6

Effects of InFat 8 Product on Bone Strength in Formula-Fed Preterm Infants: a Double-Blind, Randomized, Placebo-Controlled Trial Efficacy of InFat Blend 8

The efficacy of InFat blend 8 is investigated by a double-blind, randomized, placebo-controlled, 3 months duration trial in preterm infants. The study demonstrates the effect of formula having high proportion of palmitate in the sn-2 position (InFat™ 8 from the InFat blends list Table 1B), compared to standard vegetable oil formula on bone strength of preterm infants.

The purpose of this study is to assess the bones strength of infants by measuring the speed of sound (SOS) of an ultrasound wave along the bone. Quantitative ultrasound measurement by Sunlight Premiere® QUS device is described in Example 4.

The rising incidence of preterm births (infants born at less than 37 weeks of gestation) coupled with their improved survival as a result of highly evolving technologies, has placed an increased need to develop more innovative and cost-effective treatment modalities for preterm infants during the neonatal period and in later life.

As mentioned in the Background, Metabolic bone disease is a relatively common event in preterm infants because the greatest period of bone mineral accretion ordinarily occurs during the last trimester of pregnancy, and this is difficult to reproduce in the extra uterine environment.

Study Design:

Following screening, 60 healthy, growing, preterm infants are randomized to one of two treatment groups, 30 infants in each treatment group:
1. Formula A: The treatment formula containing InFat blend 8 with fatty acid composition presented in Table 8.
2. Formula B: The control formula containing standard vegetable oil (Table 8).

TABLE 8

| Fatty acids composition (% of weight of total fatty acids) | | |
|---|---|---|
| Fatty acid | Formula A (InFat 8) | Formula B (control) |
| C12:0 | 9 | 9 |
| C14:0 | 3 | 3 |
| C16:0 | 21 | 21 |
| C16:0 at sn-2 position | 49 | 10 |
| C18:0 | 2.5 | 2.5 |
| C18:1 | 43 | 43 |
| C18:2 | 16 | 16 |
| C18:3 | 1.5 | 1.5 |

Eligible preterm infants born at gestational age of between 32-36 weeks are randomized to one of two groups: treatment group (formula A) or control (formula B). Both groups receive the formula for 3 months and their bone strength is measured at baseline and during the study after 4, 8 and 12 weeks.

Methods:

QUS Measurements of Tibial Bone SOS:

SOS measurements of midshaft tibia are taken using Sunlight Premiere® QUS.

Results

Bone SOS measured using quantitative ultrasound technology in preterm infants fed with formula A (the invention InFat 8 formula) are expected to be significantly higher than SOS measured in infants fed with formula B (control formula) following 4 weeks, 8 weeks and 12 weeks fed. Bone SOS measurements of infants fed with formula A are likely to be increased with time in more significant pace compared to infants fed with formula B.

The expected results will likely indicate that the addition of palmitic acid in sn-2 position to infant formula results in significantly higher whole body bone strength compare to formula B.

The invention claimed is:

1. A method of increasing bone strength in a human who is at risk of impaired bone strength, comprising administering to said human who is at risk of impaired bone strength a sufficient amount of a composition,
   wherein the composition comprises a fat source,
   wherein said fat source comprises a triglyceride fat source,
   wherein the triglyceride fat source has a total fatty acid moiety composition comprised of about 15-55% palmitic acid moieties out of the total fatty acids,
   wherein the level of the total fatty acid palmitic acid moieties at a sn-2 position of the glycerol backbone is at least 30% (w/w) of the total fatty acid palmitic acid moieties, and
   when the sufficient amount of the composition is administered to the human, the bone speed of sound measured using quantitative ultrasound technology is higher in the human to whom the composition was administered than in a human to whom a placebo was administered, wherein said human is a premature infants, an obese infant, and an infant born to diabetic mother, and an infant exposed to corticosteroids.

2. The method of claim 1, wherein at least 50%, of the fatty acid moieties at the sn-1 or sn-3 positions of the glycerol backbone are unsaturated.

3. The method of claim 1, wherein said human is a premature infant.

4. The method of claim 1,
   wherein said composition further comprises a mixture of vegetable oils,
   wherein said mixture of vegetable oils comprises oils selected from the group consisting of soy, palm tree, canola, coconut, palm kernel, sunflower, corn, and rapeseed oil.

5. The method of claim 1, wherein said composition is incorporated into a food article selected from infant formula, bakery products bread, biscuits, pastries, dairy products, milk, dairy drinks, ice cream, cereal products, sauces, spreads, margarine, oils, fats, soy products, meat products, fried food products, confectionery products, candy bars, candies and chocolates, snacks, drinks and shakes, instant drink products, prepared foods for infants and young children, prepared cooked mashed vegetables and/or fruits, condiment products, and cooking oils and fats.

6. The method of claim 5, wherein said infant formula further comprises a protein source, a carbohydrate source, minerals, vitamins, carrier, diluent, additive or excipient.

7. The method of claim 1, wherein at least 35% of unsaturated fatty acid moieties at the sn-1 or sn-3 positions of the glycerol backbone are oleic acid moieties.

8. The method of claim 1, wherein at least 4% of unsaturated fatty acid moieties at the sn-1 or sn-3 positions of the glycerol backbone are linoleic acid moieties.

* * * * *

UNITED STATES PATENT AND TRADEMARK OFFICE
CERTIFICATE OF CORRECTION

PATENT NO.       : 8,623,825 B2                                                      Page 1 of 1
APPLICATION NO.  : 12/671678
DATED            : January 7, 2014
INVENTOR(S)      : Bar-Yoseph et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1013 days.

Signed and Sealed this

Twenty-second Day of September, 2015

Michelle K. Lee
*Director of the United States Patent and Trademark Office*